(12) United States Patent
Lee et al.

(10) Patent No.: US 8,821,922 B2
(45) Date of Patent: Sep. 2, 2014

(54) COMPOSITIONS AND METHODS FOR POLYMER-CAGED LIPOSOMES

(75) Inventors: Sang-Min Lee, Evanston, IL (US); SonBinh Nguyen, Evanston, IL (US); Thomas V. O'Halloran, Chicago, IL (US)

(73) Assignee: Northwestern University, Evanston, IL (US)

( * ) Notice: Subject to any disclaimer, the term of this patent is extended or adjusted under 35 U.S.C. 154(b) by 710 days.

(21) Appl. No.: 12/135,828

(22) Filed: Jun. 9, 2008

(65) Prior Publication Data

US 2008/0317840 A1 Dec. 25, 2008

Related U.S. Application Data

(60) Provisional application No. 60/933,750, filed on Jun. 8, 2007.

(51) Int. Cl.
*A61K 9/127* (2006.01)
(52) U.S. Cl.
USPC .......................................... 424/450; 435/458
(58) Field of Classification Search
None
See application file for complete search history.

(56) References Cited

PUBLICATIONS

H Kitano, Y Akatsuka, N Ise. "pH Responsive Liposomes Which Contain Amphiphiles Prepared by Using Lipophilic Radical Initiator." Macromolecules, 1991, vol. 24, pp. 42-46.*
Biochemistry 462a. http://www.biochem.arizona.edu/classes/bioc462/462a/NOTES/LIPIDS/Lipids_membranes.html. Apr. 20, 2002 (as of internet archive), 7 pages.*
S Vinogradov. "The Second Annual Symposium on Nanomedicine and Drug Delivery: exploring recent developments and assessing major advances." Aug. 19-20, 2004, Polytechnic University, Brooklyn, NY, USA. Author Manuscript Included, 5 pages.*
TLM ten Hagen, S Hoving, G Ambagtsheer, ST van Tiel, AMM Eggermont. "Lack of efficacy of Doxils in TNF-a-based isolated limb perfusion in sarcoma-bearing rats." British Journal of Cancer, 2004, vol. 90, pp. 1830-1832.*

* cited by examiner

*Primary Examiner* — Frederick Krass
*Assistant Examiner* — Isaac Shomer
(74) *Attorney, Agent, or Firm* — Casimir Jones S.C.

(57) ABSTRACT

The present invention provides liposomal compositions and methods of using such compositions in vitro and in vivo. In particular, the present invention provides stable, polymer-caged liposomes comprising a pH responsive delivery mechanism for delivery of nucleic acids, peptides, small molecules, drugs, etc. in vitro and in vivo.

15 Claims, 11 Drawing Sheets

US 8,821,922 B2

COMPOSITIONS AND METHODS FOR POLYMER-CAGED LIPOSOMES

The present application claims priority to U.S. Provisional Application Ser. No. 60/933,750, filed Jun. 8, 2007, which is herein incorporated by reference in its entirety.

This invention was made with government support under Grant Nos. DMR-0094347 and EEC-0647560 awarded by The National Science Foundation and Grant No. U54CA119341 awarded by the National Institute of Health's National Cancer Institute Center for Cancer Nanotechnology Excellence and P30CA060553 core grant awarded by the National Institute of Health. The government has certain rights in the invention.

FIELD OF THE INVENTION

The present invention provides liposomal compositions and methods of using such compositions in vitro and in vivo. In particular, the present invention provides stable, polymer-caged liposomes comprising a pH-responsive delivery mechanism for delivery of nucleic acids, peptides, small molecules, drugs, etc. in vitro and in vivo.

BACKGROUND OF THE INVENTION

Liposomes are self-assembled vesicles having a spherical bilayer structure surrounding an aqueous core domain. Due to their intrinsic biocompatibility and ease of preparation, several liposomal drugs have been approved (Torchilin, 2005, Nat. Rev. Drug Discov. 4:145-160). In addition, modified liposomes on the nanoscale (20-200 nm) have been shown to have excellent pharmacokinetics profiles for the delivery of nucleic acids, proteins, and chemotherapeutic agents such as doxorubicin (Papahadjopoulos et al., 1991, Proc. Natl. Acad. Sci. 88:11460-11464; Eliaz et al., 2001, Cancer Res. 61:2592-2601). However, major drawbacks of liposome-based drug carriers include their instability and the lack of tunable triggers for drug release. As such, there have been several attempts at enhancing the properties of liposomes (Torchilin, 2005; Ringsdorf et al., 1988, Angew. Chem. Int. Ed. 27:113-158). Incorporation of polymerizable lipid amphiphiles leads to crosslinked liposomes with higher stability (O'Brien et al., 1998, Acc. Chem. Res. 31:861-868). Unfortunately, every lipid system would require a specific polymerizable amphiphile, making this approach synthetically cumbersome. In addition, the crosslinks are often too stable to allow for controllable release of the payload. To provide a combination of stability and modification generality, hydrophilic polymers such as poly(ethylene glycol) (PEG) (Papahadjopoulos et al., 1991) and poly(N-isopropylacrylamide) (Ringsdorf et al., 1988) have been added to liposomes. However, these modifiers can easily dissociate from the liposome surface, returning them to the unstable state (Adlakha-Hutcheon et al., 1999, Biotechnol. 17:775-779; Silvius et al., 1993, Biochem. 32:3153-3161; Holland et al., 1996, Biochem. 35:2618-2624).

As such, what are needed are liposomal constructs that will accommodate a wide variety of payloads (e.g., nucleic acids, peptides, small molecules, drugs, etc.), maintain stability, and deliver the payload to the intended location.

SUMMARY OF THE INVENTION

The present invention provides liposomal compositions and methods of using such compositions in vitro and in vivo. In particular, the present invention provides stable, polymer-caged liposomes comprising a pH-responsive delivery mechanism for delivery of nucleic acids, peptides, small molecules, drugs, etc. in vitro and in vivo.

Certain illustrative embodiments of the invention are described below. The present invention is not limited to these embodiments.

In some embodiments, the present invention provides compositions comprising a pH-responsive stable polymer-caged liposome. In particular embodiments, the pH-responsive stable polymer-caged liposome (PCL) comprises: i) a bare liposome, ii) a membrane anchoring group (e.g., attached to a linker), iii) a crosslinkable polymer, and iv) a bifunctional crosslinking molecule that crosslinks with the crosslinkable polymer. In further embodiments, the liposome is a pH-responsive delivery system for payloads. In other embodiments, the liposome comprises a payload selected from the group consisting of: a drug, small molecules, a nucleic acid, and a peptide. In further embodiments, the pH-responsive stable polymer-caged liposome comprises a membrane anchoring group. In particular embodiments, the PCL further comprises a linker that may also be crosslinkable, wherein the anchoring group is attached to the linker. In other embodiments, the PCL further comprises a targeting ligand, wherein the targeting ligand is operably connected to either the linker, the crosslinkable polymer, the bifunctional crosslinking molecule, or the membrane-anchoring group. In further embodiments, the PCL comprises a detectable molecule, wherein the detectable molecule is operably connected to the membrane anchoring group. In some embodiments, the PCL further comprises a drug molecule, wherein the drug molecule is operably connected to the membrane anchoring group. In other embodiments, the membrane anchoring group comprises cholesterol-terminated poly(acrylic acid).

In certain embodiments, the present invention provides methods for transfecting cells comprising: a) providing: i) a pH-responsive, stable polymer-caged liposome, ii) a eukaryotic cell, iii) a nucleic acid, b) complexing the liposome with the nucleic forming a liposome with a nucleic acid payload, c) transfecting the liposome with a nucleic acid payload into the eukaryotic cell such that release of the payload is realized at a particular pH. In some embodiments, the transfecting is performed in vitro in mammalian cells or other type of cell. In further embodiments, the transfecting is performed in vivo in a subject.

In certain embodiments, the present invention provides delivery systems comprising a bare liposome, a membrane-anchoring group (e.g., attached to a linker), a crosslinkable polymer, and a bifunctional crosslinking molecule that crosslinks with the crosslinkable polymer, wherein the delivery system delivers a payload to a cell. In some embodiments, the delivery system is further pH-responsive such that the payload is deliver to the cell bases on the pH in the cell. In other embodiments, the payload is from the group consisting of nucleic acids, small molecules, peptides, proteins, or drugs.

In some embodiments, the present invention provides methods of treatment comprising: administering a pH-responsive stable polymer-caged liposome to a subject, wherein the pH-responsible stable polymer-caged liposome comprises a therapeutic payload, and wherein the administering is under conditions such that the payload is released in the subject resulting in at least a partial therapeutic effect. In certain embodiments, the payload comprises a drug for treating a disease.

In certain embodiments, the present invention provides methods of treatment comprising: administering a pH-responsive stable polymer-caged liposome to a subject, wherein the pH-responsiveble stable polymer-caged liposome comprises one of more of the following groups: a therapeutic payload, one or more types of targeting ligands, one or more types of detectable molecules, and wherein the administering is under conditions such that the payload is released in the subject resulting in at least a partial therapeutic effect.

In some embodiments, the present invention provides for polymer-caged liposomes. In some embodiments, the polymer-caged liposomes comprise a membrane-anchoring group attached to a linker. For example, cholesterol and derivatives thereof anchor in bilayer membranes and find utility as anchoring groups with compositions of the present invention and polyacrylic acid is exemplary of a linker. In some embodiments, the polymer-caged liposomes further comprise a short, potentially crosslinkable, polymer with constituents for binding said linker through, for example, amide bonds as exemplified herein. Amide bond can be formed with said short polymer via a bifunctional crosslinking molecule, thereby producing a polymer-caged liposome.

In some embodiments, a polymer-caged liposome (PCL) of the present invention comprises a payload, such as a drug, small molecule, nucleic acid, peptide and the like for release either in a tissue specific manner or systemically. For example, anthracycline-based chemotherapeutic agents such as doxorubicin, arsenic trioxide inorganic drug as a form of $NiHAsO_3$, and nucleoside-based prodrugs such as 8-amino adenosine and 8-chloro adenosine, can all be incorporated into the PCL. The resulting payload-incorporated PCL, when linked to a targeting ligand (for instance, cyclic peptides, FAB fragments, monoclonal antibodies, etc. . . . ), may be made specific and delivers the payload to the ligand's target. In some embodiments, the PCL comprises a fluorophore functional group, or other detectable or imaging component. For example, a fluorophore (or an MRI contrasting agent) can be bound to a PCL and then subsequently be, for example, used in in vitro or in vivo localization of a PCL, pH studies, and other such research, diagnostic, or therapeutic endeavors.

In some embodiments, the PCLs of the present invention provide a pH-sensitive delivery system such that payload delivery is triggered by low (acidic) or high (basic) pH. In some embodiments, PCLs of the present invention are stable as compared to basic liposomes or polymer-incorporated liposomes. Stability includes, but is not limited to, the ability to maintain integrity (e.g., not leak), transfectivity, and/or payload delivery mechanisms upon lyophilization or other physically altering preparatory methods, exposure to biological sera (e.g., bovine, fetal calf, human, etc.), etc. as compared to bare liposomes or polymer-incorporated liposomes.

In some embodiments, the present invention provides methods for delivery of payloads in subjects in vivo or otherwise in vitro. For example, methods of the present invention comprise the complexing of liposomes with a payload for delivery of a therapeutic drug in vivo to a subject in need of treatment of a disease, disorder, etc. In some embodiments, methods of the present invention comprise the delivery of the compositions as described herein in vivo into non-human and human subjects. In some embodiments, the transfection methods comprising compositions of the present invention allow for pH-triggered delivery of payload compounds. Such methods find utility for example, for developing drug delivery protocols, drug discovery, and basic research.

In some embodiments, the present invention provides methods for in vitro use of PCLs and associated payloads, for example in tissue culture or in a cell lysate (e.g., bacterial cell, yeast, mammalian cell, etc.). In some embodiments, in vitro methods further comprise the pH-responsive release of PCL payload compounds into the environment.

DESCRIPTION OF THE FIGURES

FIG. 1D shows an exemplary schematic depiction of the stages for producing polymer-caged liposomes.

DEFINITIONS

Figure 1:
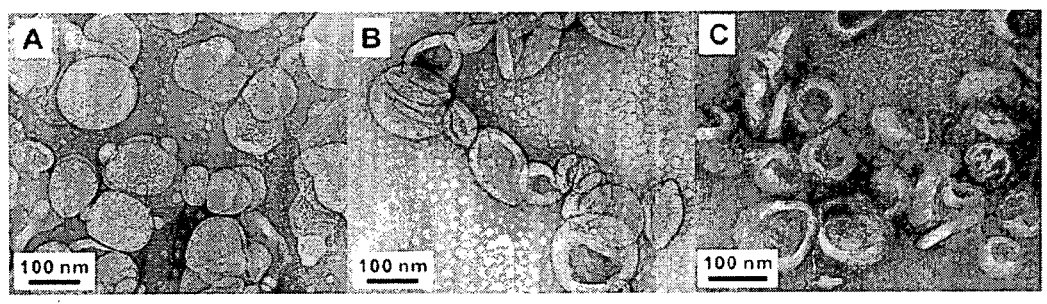
FIG. 1 shows an exemplary depiction of polymer-caged liposomes and associated transmission electron microscope (TEM) images exemplifying each stage of synthesis: (A) bare liposomes (BLs), (B) polymer-incorporated liposomes (PILs), and (C) polymer-caged liposomes (PCLs). All samples were negatively stained with 4% uranyl acetate. Both wholly spherical (A) and indented spherical morphologies (B and C) are observed in liposomal TEM and are functions of the sample preparation.
Figure 1:
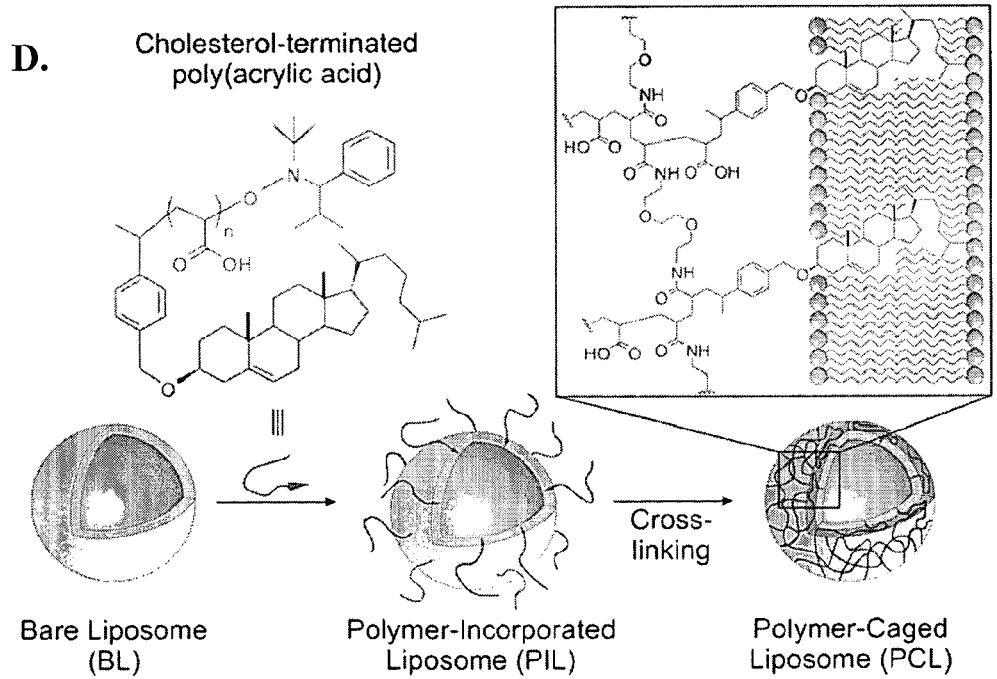

As used herein, the term "subject" refers to any animal (e.g., a mammal), including, but not limited to, humans, non-human primates, rodents, and the like, which is to be the recipient of a particular treatment. Typically, the terms "subject" and "patient" are used interchangeably herein in reference to a human subject.

As used herein, the term "non-human animals" refers to all non-human animals including, but are not limited to, vertebrates such as rodents, non-human primates, ovines, bovines, ruminants, lagomorphs, porcines, caprines, equines, canines, felines, aves, etc.

As used herein, the term "cell culture" or "tissue cell culture" refers to any in vitro culture of cells. Included within this term are continuous cell lines (e.g., with an immortal phenotype), primary cell cultures, transformed cell lines, finite cell lines (e.g., non-transformed cells), and any other cell population maintained in vitro.

As used herein, the term "in vitro" refers to an artificial environment and to processes or reactions that occur within an artificial environment. In vitro environments can consist of, but are not limited to, test tubes and cell culture. The term "in vivo" refers to the natural environment (e.g., an animal or a cell) and to processes or reaction that occur within a natural environment.

The terms "payload" refers to any chemical entity, pharmaceutical, drug (such drug can be, but not limited to, a small molecule, an inorganic solid, a polymer, or a biopolymer), small molecule, nucleic acid (e.g., DNA, RNA, siRNA, etc.), protein, peptide and the like that is complexed with a liposomal formulation described in the present invention. A payload also encompasses a candidate (e.g., of unknown structure and/or function) for use to treat or prevent a disease, illness, sickness, or disorder of bodily function and includes, but is not limited to, test compounds that are both known and potential therapeutic compounds. A test compound can be determined to be therapeutic by screening using the screening methods of the present invention.

The term "nucleic acid" refers to a polymer of nucleotides, or a polynucleotide, as described above. The term is used to designate a single molecule, or a collection of molecules. Nucleic acids may be single-stranded or double-stranded, and may include coding regions and regions of various control elements, and are either deoxyribonucleotides or ribonucleotides.

The terms "protein" and "polypeptide" and "peptide" refer to compounds comprising amino acids joined via peptide bonds and are used interchangeably.

As used, the term "eukaryote" refers to organisms distinguishable from "prokaryotes." It is intended that the term encompass all organisms with cells that exhibit the usual characteristics of eukaryotes, such as the presence of a true nucleus bounded by a nuclear membrane, within which lie the chromosomes, the presence of membrane-bound organelles, and other characteristics commonly observed in eukaryotic organisms. Thus, the term includes, but is not limited to such organisms as fungi, protozoa, and animals (e.g., humans).

The term "transfection" as used herein refers to the introduction of foreign nucleic acids (e.g., DNA or RNA) into eukaryotic cells. Transfection may be accomplished by a variety of means known to the art including, but not limited to, calcium phosphate-DNA co-precipitation, DEAE-dextran-mediated transfection, polybrene-mediated transfection, electroporation, microinjection, liposome fusion, liposomal, lipofection, protoplast fusion, retroviral infection, and biolistics. Embodiments of the present invention comprise liposomal transfection.

DETAILED DESCRIPTION OF THE INVENTION

Certain illustrative embodiments of the invention are described below. The present invention is not limited to these embodiments.

Liposomal complexes are attractive vehicles for delivery of payloads including, but not limited to, compounds (e.g., therapeutic and otherwise) such as drugs, nucleic acids, peptides, and the like. However, major drawbacks of liposome-based delivery systems include their instability and the lack of tunable triggers for drug release. As such, there have been several attempts at enhancing the properties of liposomes; however, none of them have reached potential as viable delivery vehicles. In developing embodiments of the present invention, a general "drop-in" strategy that allows for long-term stabilization of virtually any liposome system via a biocompatible polymer cage was discovered.

Crosslinking of surface functional groups in polymer nanoparticles (PNPs) have been shown to prevent the dissociation of polymer components (Huang et al., 1997, J. Am. Chem. Soc. 119:11653-11659). In addition, highly functionalized polymer nanomaterials can be engineered to change shape via external stimuli such as pH and temperature (Nayak et al., 2005, Angew. Chem. Int. Ed. 44:7686-7708; Hawker et al., 2005, Science, 309:1200-1205). The present invention provides embodiments for the combination of both of these design features to arrive at a single polymer amphiphile that stabilizes any liposome system while allowing for additional attributes such as tunable drug-releasing properties and targeting ability. In particular, it is demonstrated herein that a cholesterol-terminated poly(acrylic acid) (Chol-PAA), or functionally related components, can be readily inserted (e.g. a "drop in" moiety) into a known liposome system and then crosslinked to stabilize the bilayer membrane (FIG. 1). The present invention is not limited to Chol-PAA as a bilayer stabilizer. In some embodiments, as an alternative to cholesterol-based anchoring groups, phospholipid-based amphiphiles such as distearoyl phosphatidyl-ethanolamine (DSPE) can also be used (Papahadjopoulos et al., 1991, Proc. Natl. Acad. Sci. 88:11460-11464, herein incorporated by reference).

There are three factors useful for selecting preferred compounds for inserting into a liposome system for crosslinking and stabilization of the bilayer membrane. First, the compound comprises a membrane-anchoring group; for example, cholesterol or its derivatives associated with a linker as exemplified in the embodiments described herein. Second, a linker interacts with a short polymer with substituents capable of being coupled by a chemical bond (e.g., amide, etc.); for example, the carboxylates of the polyacrylic acid moiety as exemplified in the embodiments described herein. Third, a crosslinker molecule (e.g., bifunctional) capable of forming crosslinking bonds (e.g., amine crosslinking amide bonds) is included in the composition for linking the compositions together.

Figure 2:
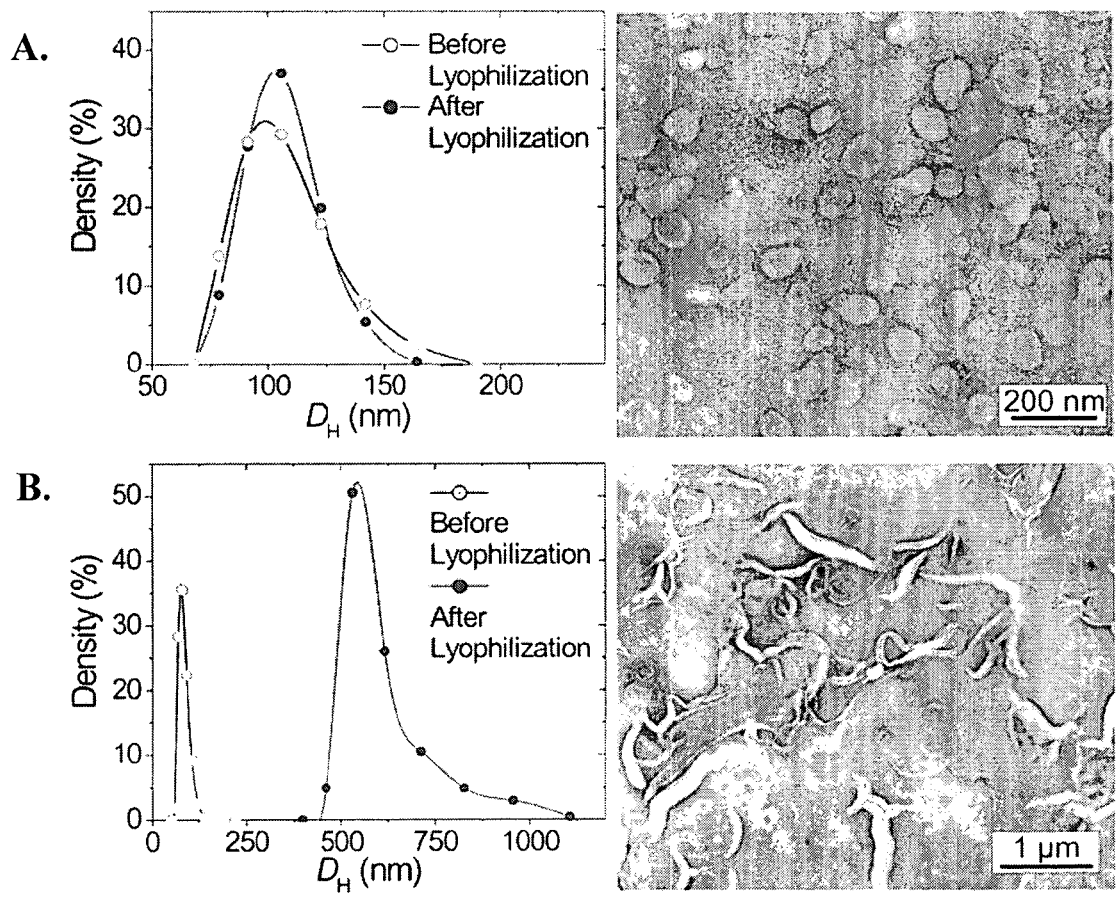
FIG. 2 shows the enhanced stability of polymer-caged liposomes (A) and bare liposomes (B). Shown in the left hand side of each panel is a plot of the average hydrodynamic diameter of these respective liposomes before and after lyophilization, as measured by dynamic light scattering. Shown in the right hand side of each panel is the TEM image of these respective liposomes after lyophilization

The resulting Polymer-Caged Liposomes (PCLs) are highly stable and can be lyophilyzed into powder forms and redispersed without loss of structural coherence (FIG. 2). They can also be induced to release a payload under acidic conditions. As such, applications include, but are not limited to, in vitro and in vivo environment-specific nanoscale delivery vehicles; for example, for therapeutic, diagnostic, or research, delivery of drugs, nucleic acids, small molecules, peptides, and the like.

Figure 3:
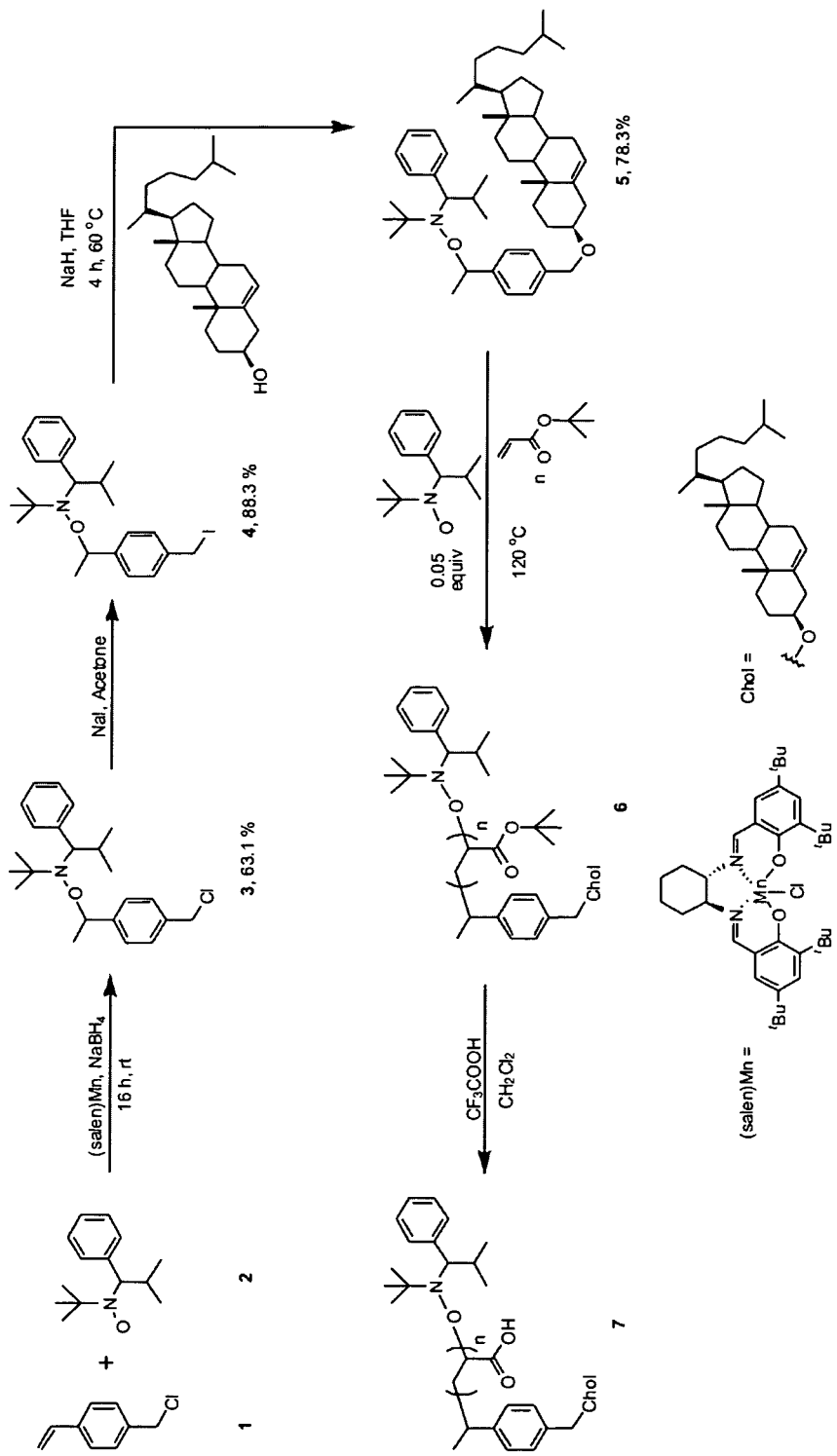
FIG. 3 shows an exemplary synthesis of the cholesterol-terminated poly(acrylic acid) that is used in the fabrication of PILs and PCLs.

In one embodiment of the present invention, narrowly dispersed cholesterol-terminated poly(acrylic acid) ($M_n$=2.5 kDa, $M_w/M_n$=1.1) was synthesized via nitroxide-mediated controlled radical polymerization (Benoit et al., 1999, J. Am. Chem. Soc. 121:3904-3920) of tert-butyl acrylate followed by hydrolysis (FIG. 3). Poly(acrylic acid) was employed as an exemplary hydrophilic polymer due to its biocompatibility and easily crosslinkable carboxylate group. The cholesterol end group acted as a single anchor to eliminate the possible aggregation often seen with polymers including multi-anchor groups (Hara et al., 1998, J. Supramol. Sci. 5:777-781).

Figure 5:
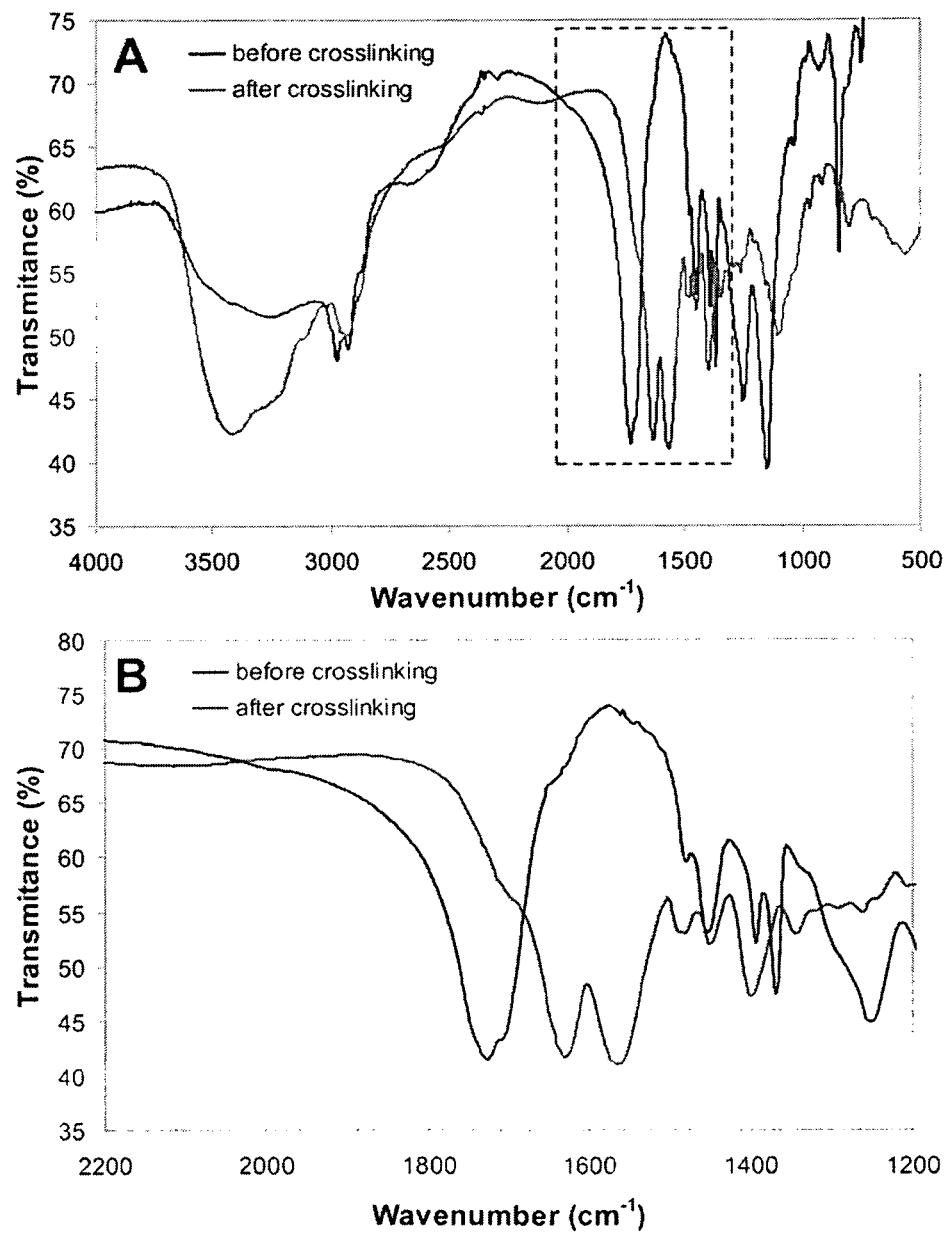
FIG. 5 shows: (A) The full FT-IR spectra of PCLs before and after crosslinking and (B) the zoomed-in FT-IR spectra of PCLs before and after crosslinking.
Figure 6:
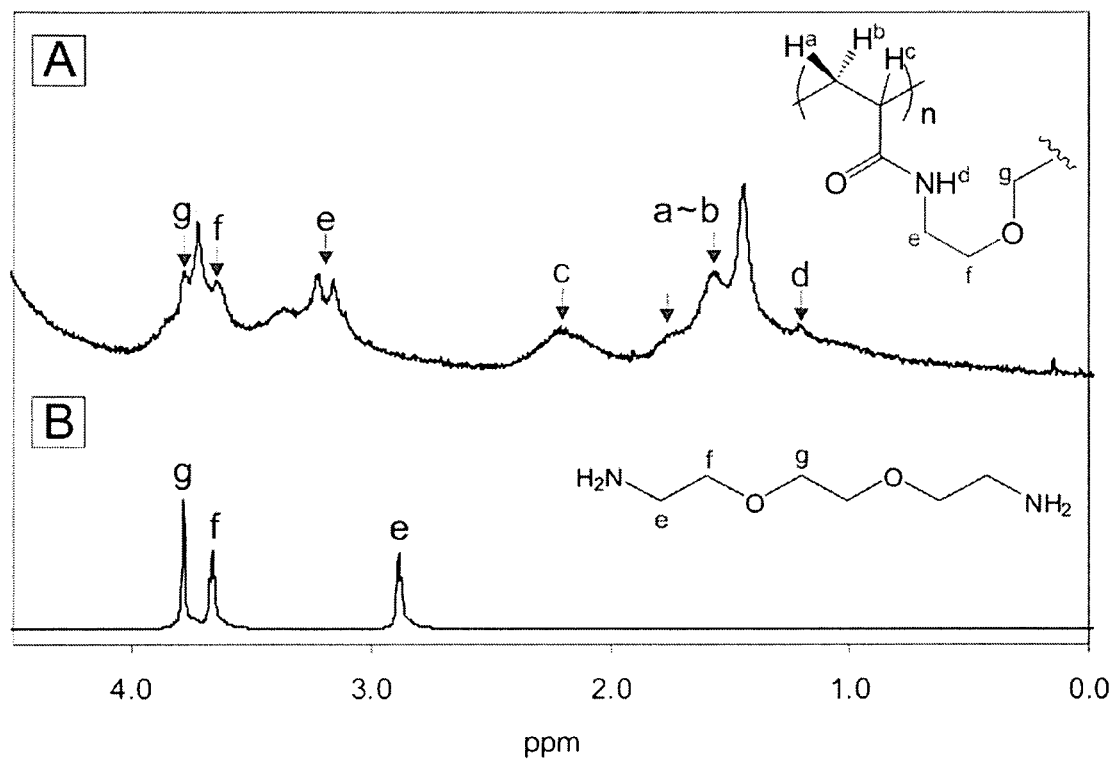
FIG. 6 shows: (A) The water-suppressed $^1$H NMR spectrum of PCLs; (B) The $^1$H NMR spectrum of the free diamine crosslinker. After crosslinking, proton resonance 'e' was shifted to downfield to 3.2 ppm (from 2.9 ppm).
Figure 7:
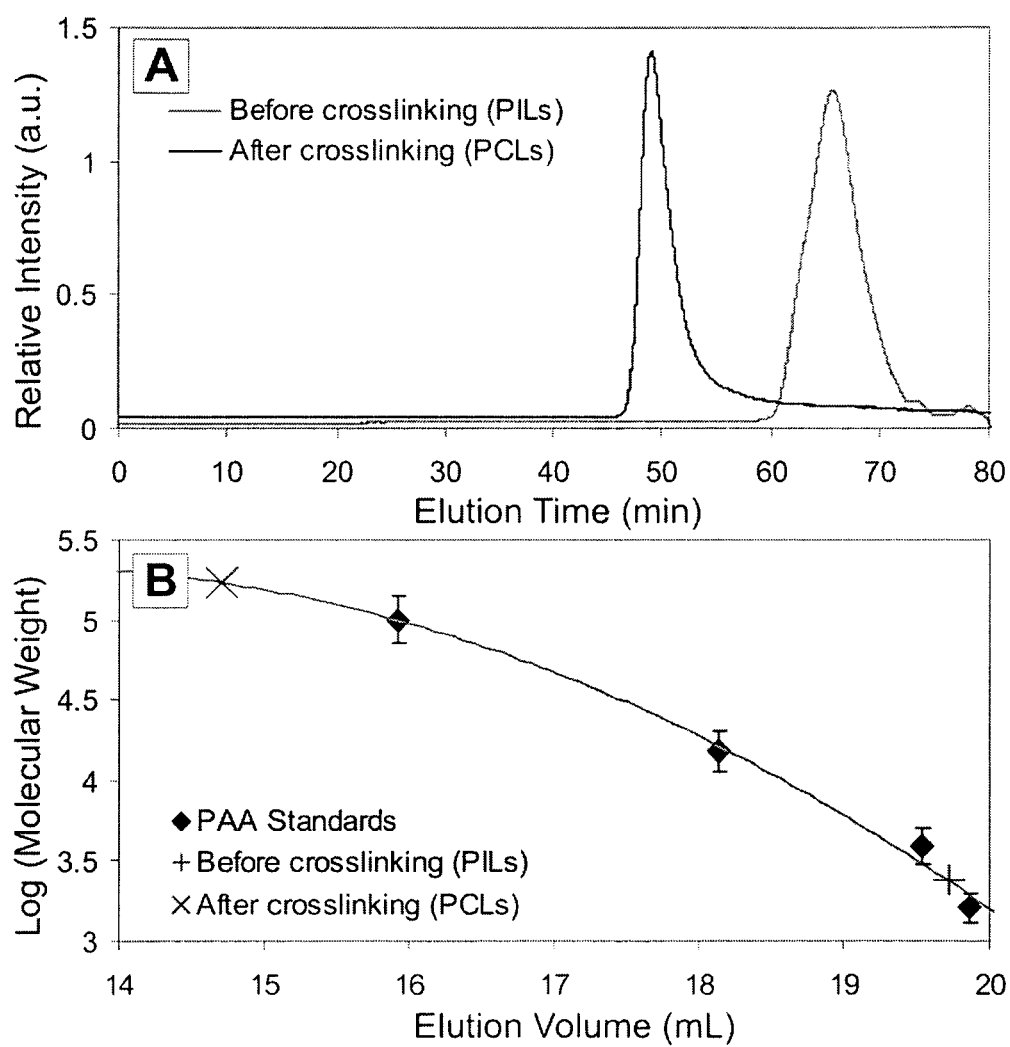
FIG. 7 shows: (A) The gel-filtration chromatogram of polymer-incorporated liposomes before and after crosslinking; (B) The semi-logarithmic plot of polymer molecular weight versus elution volume for the polymer components in PILs and PCLs against a series of water-soluble polymer standards.

Chol-PAA (10 mol % compared to the total amount of lipids) was mixed with a solution of bare liposomes (BLs, $D_H$=82±14 nm, PDI=0.046±0.021 via dynamic light scattering (DLS), prepared from dipalmitoylphosphatidylcholine (DPPC), dioleoyl-phosphatidylglycerol (DOPG) and cholesterol with molar ratio of 51.4:3.6:45, FIG. 1A) and incubated overnight to yield polymer-incorporated liposomes (PILs, FIG. 1B) (Liu et al., 1993, J. Am. Chem. Soc. 115:708-713). After incubation, only particles with increased mean $D_H$ (93±15 nm, PDI=0.047±0.016) were observed (FIG. 4), suggesting the homogeneous formation of PILs. Crosslinking of the poly(acrylic acid) moieties on the surface of PILs was achieved using 2,2'-(ethylenedioxy)bis(ethylamine). The formation of amide bond in the resulting PCLs (FIG. 1C) was confirmed by FT-IR (FIG. 5) and water-suppressed $^1$H-NMR spectra (FIG. 6). The apparent molecular weight of the crosslinked polymer-shell increased (FIG. 7), indicating that significant cross-linking has occurred (PDI=0.070±0.028).

Figure 8:
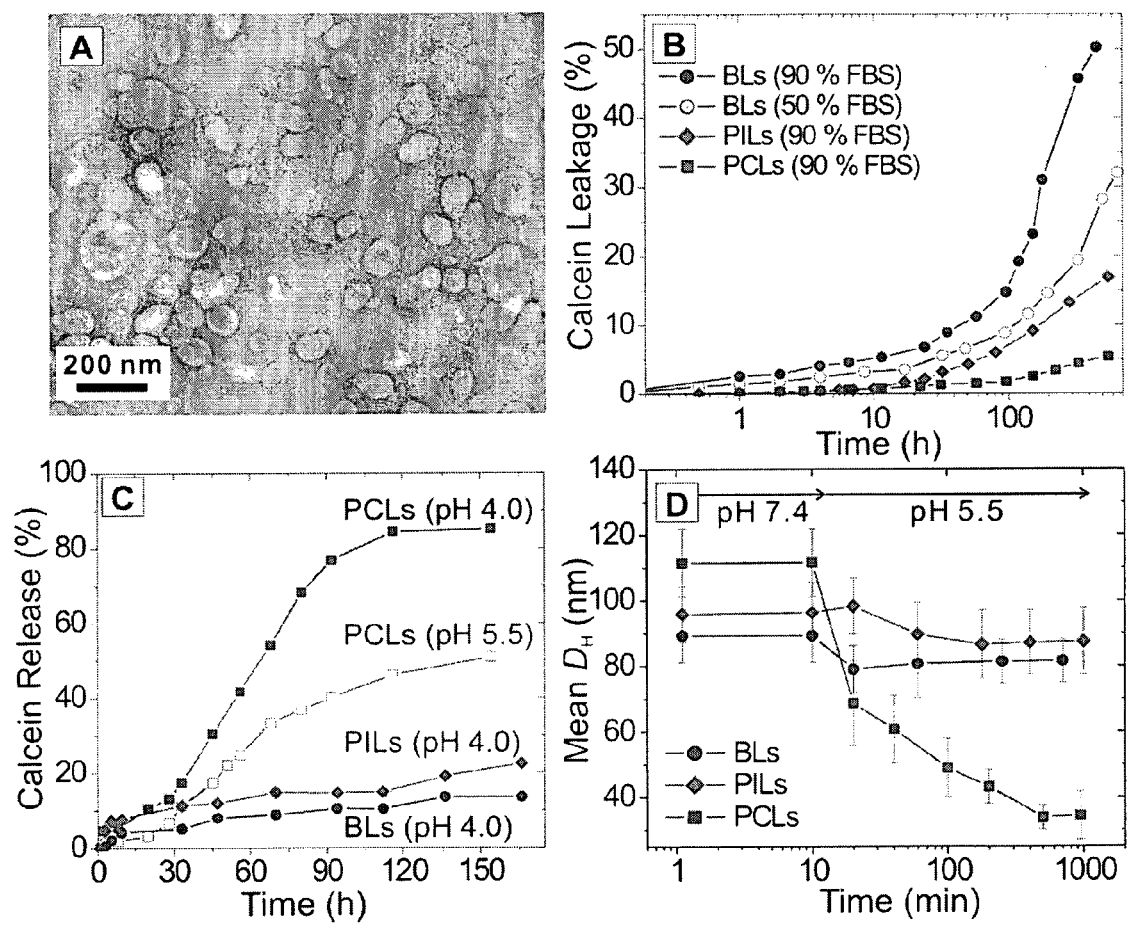
FIG. 8 shows: (A) The TEM image of PCLs after freeze-drying and rehydration; (B) The calcein-leakage profile of BL, PIL, and PCL at 37° C. in fetal bovine serum (FBS); (C) The acid-triggered calcein release profile at 37° C. and; (D) The temporal evolution of mean $D_H$ in pH 7.4 and 5.5.

As exemplified in the embodiments, PCLs of the present invention are stable and their spherical structures were fully preserved after freeze-drying and rehydration (FIG. 2, FIG. 8A). In contrast, the same treatment completely destroyed the spherical BLs (FIG. 2), presumably via an induced phase transition to the thermodynamically favorable lamellar structure (Szleifer et al., 1998, Proc. Natl. Acad. Sci. 95:1032-1037) upon loss of the supporting aqueous core. The stability of the exemplary PCLs under the lyophilization/rehydration process demonstrates that they can be stored on a long-term basis, a desirable feature in delivery applications.

For in vivo applications, it is derisible that drug carrier vesicles possess, for example, high plasma stability. Accordingly, the stability of a calcein-encapsulated sample of the PCLs was evaluated against fetal bovine serum (FBS) at 37° C. following a procedure described by Allen et al. (1980, Biochim. Biophys. Acta. 597:418-426). As calcein's fluorescence is self-quenched under the high concentrations found in intact liposomes, its leakage due to vesicle rupture is readily observed. Remarkably, only a minute leakage of calcein (~5%) was observed from the PCLs after 500 h, an order of magnitude less than the leakage in BLs (FIG. 8B). The inhibition of PCL rupture is attributed to the steric barrier provided by the crosslinked polymer-shell. Although incorporation of PEG-conjugated phospholipids into liposomes has been reported to sterically stabilize the resulting vesicles (Papahadjopoulous et al., 1991), long-term stability was low due to the rapid dissociation of the water-soluble polymer-attached lipids from the bilayer membrane (Adlakha-Hutcheon et al., 1999). In a similar manner, the non-crosslinked Chol-PAAs in exemplary PILs dissociate easily into solution during prolonged incubation and lead to increased calcein leakage from the unprotected vesicles. Calcein leakage from PILs was comparable to that of PCLs during the initial 10 h of incubation (~0.7% leakage); however, it began to increase steeply afterward. Similar lag periods (several minutes to a few hours) prior to accelerated destabilization were reported in PEG-conjugated liposomes (Holland et al., 1996). In this sense, the crosslinked polymer-shell in the exemplary PCLs greatly reduces polymer dissociation and results in a substantial increase in their long term stability.

Given that a significant number of carboxylic acid groups remained on the crosslinked polymer-shell of the exemplary PCLs, it was contemplated that their shapes, and consequently their payload-release ability, can be manipulated with pH. Hence, a pH-dependent release profile was observed from the exemplary calcein-encapsulating PCLs, such as when they were subjected to acidic conditions at 37° C., 84% and 50% release were achieved after 150 h at pH 4.0 and 5.5, respectively (FIG. 8C). In comparison, relatively slow release in BLs and PILs were observed at pH 4.0 over the same period. It has been contemplated that low pH induces a random-coil-to-globular phase change for polymers in the PCL membrane due to increased hydrophobic interactions between polymer chains (Nayak et al., 2005). At the same time, the protonated acrylate groups in PCLs can hydrogen-bond to the phosphodiester head groups of the lipid molecules in the membrane, decreasing lipid-lipid interactions responsible for membrane stabilization (Seki et al., 1984, Macromolecules 17:1692-1698). Both of these effects can lead to a collapse of the crosslinked shell and a subsequent compression/rupture of the PCL core. At a minimum, they can perturb the membrane structure and induce the formation of pores that are sufficiently large to allow for the leakage of the calcein contents (Chung et al., 1996, Macromolecules 29:4636-4641). Evidences for the collapsed crosslinked shells are found by monitoring the mean $D_H$ of PCLs as the solution pH is suddenly reduced to 5.5 from 7.4 (FIG. 8D), a rapid decrease of mean $D_H$ commenced and continued to decrease over 500 min (69% compression). As controls, BLs and PILs did not show significant decrease in mean $D_H$ at pH 5.5.

Figure 9:
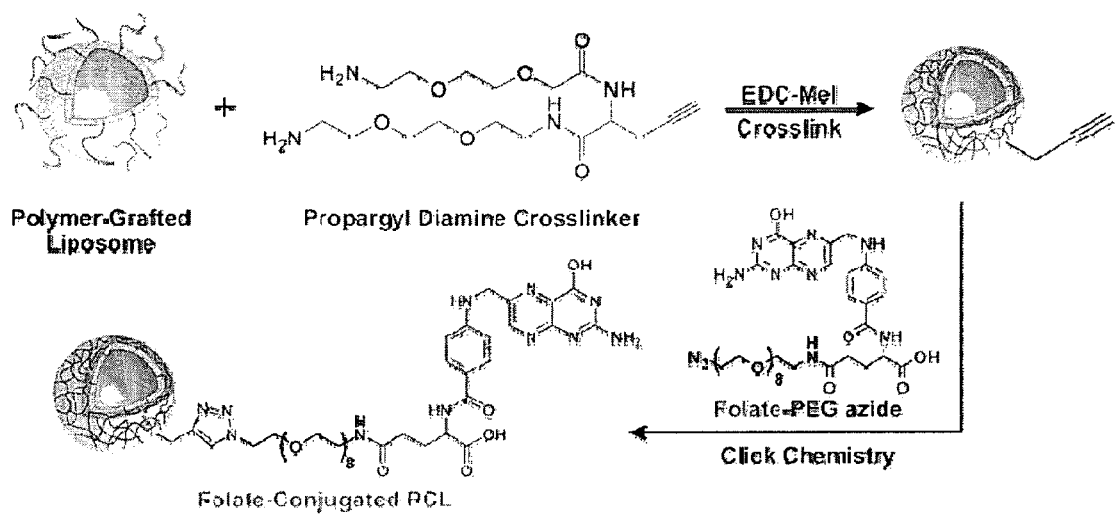
FIG. 9 shows an exemplary schematic for the synthesis of folate-conjugated PCLs.
Figure 10:
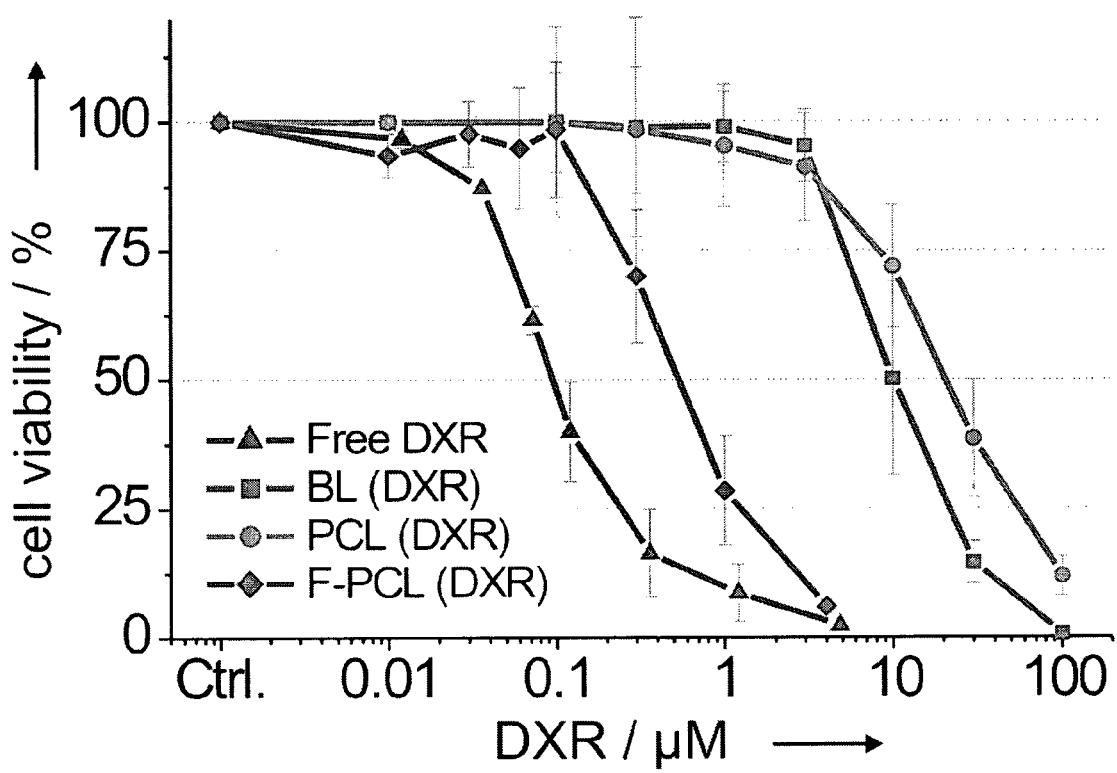
FIG. 10 shows a cytotoxicity assays demonstrating the efficacy of doxorubicin (DXR)-loaded liposomes against KB cells. $IC_{50}$ values are 0.1 µM for free DXR, 10 µM for doxorubicin-loaded bare liposomes (BL-DXR), 21 µM for doxorubicin-loaded PCLs (PCL-DXR), and 0.55 µM for folate-conjugated, doxorubicin-loaded PCLs (F-PCL-DXR). Cytotoxictity assay were conducted using the Guava Via-Count Assay system.

As a demonstration of target incorporation into PCL, folic acid (Vitamin Bg), a known small-molecule targeting ligand for cancer cells, was linked to doxorubicin-loaded PCLs via Cu(I)-catalyzed [2+3]cycloaddition reaction (click chemistry). Initially, acetylene-functionalized PCLs were prepared using propargyl-modified diamine cross-linkers. Azido-poly(ethylene glycol)-modified folates were then conjugated to the acetylene groups on the surface of PCLs catalyzed by Cu(I) (FIG. 9) to present folate groups on the PCL surface. The folate conjugation to doxorubicin-loaded PCLs indeed increased the drug efficacy against cancer cells as shown through an in vitro model study against KB epidermoid carcinoma cells. While encapsulation of doxorubicin-loaded bare liposome by a cross-linked polymer shell increased the $IC_{50}$ value of the encapsulated drug from 10 μM to 21 μM due to the stabilization of carriers, folate conjugation to doxorubicin-loaded PCLs substantially reduced this value to 0.55 μM, indicating enhanced drug uptake and efficacy (FIG. 10).

Figure 11:
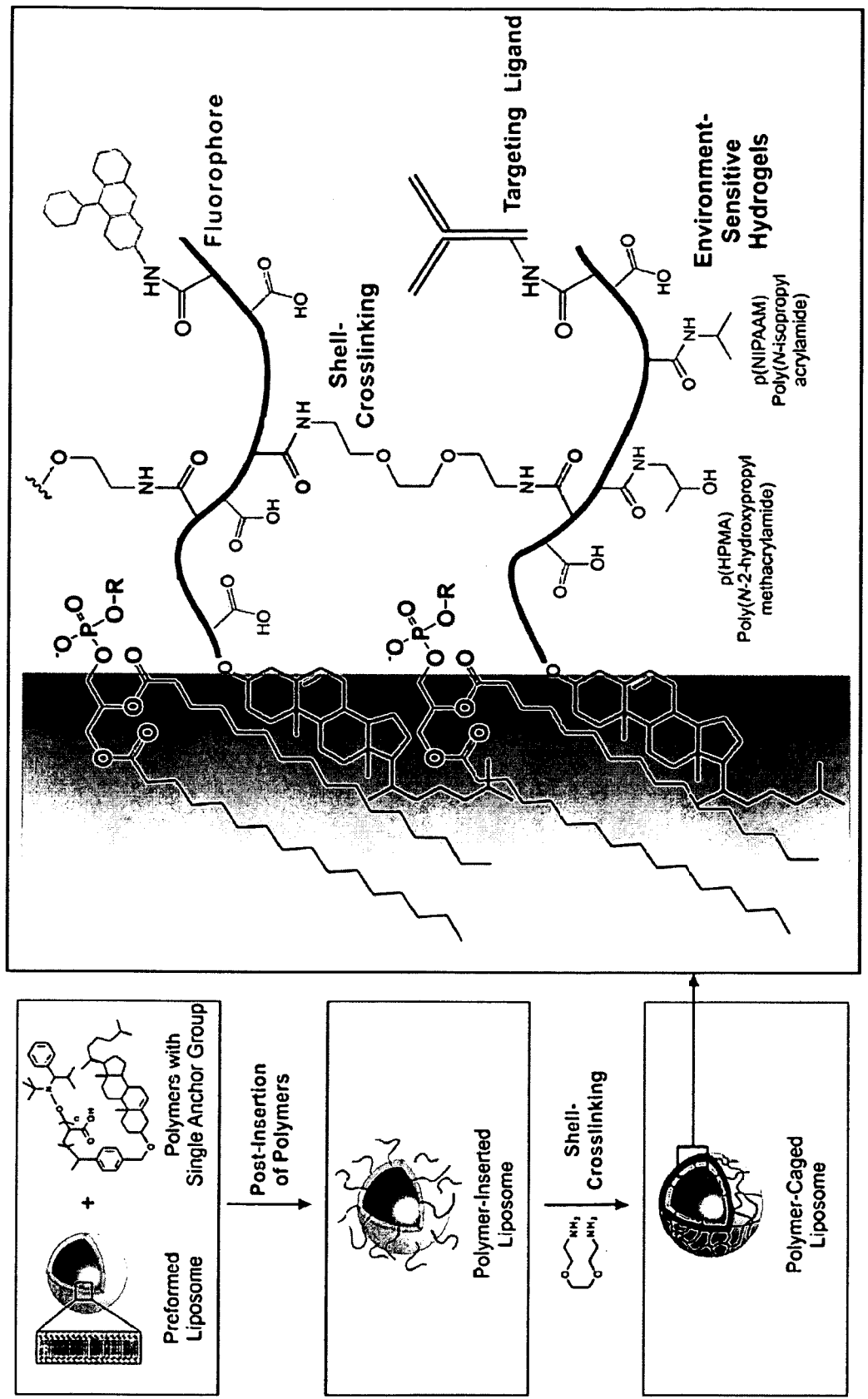
FIG. 11 shows the exemplary functionalization of a polymer-caged liposome with a fluorophore and a targeted ligand.

As such, polymer-caged liposomes as exemplified in embodiments of the present invention were readily prepared from preformed liposomes and a cholesterol-functionalized poly(acrylic acid) additive via a facile "drop-in" procedure. The highly enhanced stability and tunable pH-sensitive responses of these exemplary materials are made possible, for example, by the environmental responsive properties of the encapsulating polymer shell. As such, it is demonstrated herein that compositions of the present invention can be used to modify many clinically relevant liposome-based drug delivery systems, including inorganic drugs (Chen et al., 2006, J. Am. Chem. Soc. 128:13348-13349). In addition, as the crosslinked polymer shell still possesses un-modified carboxylic acid groups; for example, it can be further functionalized with antibody- and ligand-based targeting groups using "post-particle-formation modification" strategies (Bertin et al., 2006, J. Am. Chem. Soc. 128:4168-4169) as shown in FIG. 11.

EXPERIMENTAL

The following examples are provided in order to demonstrate and further illustrate certain preferred embodiments and aspects of the present invention and are not to be construed as limiting the scope thereof.

Fourier-transformed nuclear magnetic resonance (NMR) spectroscopy was performed on a Varian INOVA-500 MHz spectrometer. Chemical shifts of $^1$H NMR spectra are reported in ppm against residual solvent resonance as the internal standard ($CDCl_3$=7.27 ppm, acetone-$d_6$=2.05 ppm, $D_2O$=4.80 ppm). $^1$H NMR data are reported as follows: chemical shift (multiplicity (s=singlet, d=doublet, t=triplet, q=quartet, and m=multiplet), integration, assignments). Electrospray-ionization mass spectrometric (ESI-MS) data were obtained on a Micromass Quattro II triple quadrupole mass spectrometer. Phosphorus concentration was determined using a Varian Vista MPX simultaneous inductively coupled plasma optical emission spectrometer (ICP-OES).

Polymer molecular weights were measured relative to polystyrene standards on a Waters gel-permeation chromatograph (GPC) equipped with Breeze software, a 717 autosampler, Shodex KF-G guard column, KF-803L and KF-806L columns in series, a Waters 2440 UV detector, and a 410 RI detector. HPLC-grade THF was used as an eluent at a flow rate of 1.0 mL/min and the instrument was calibrated using polystyrene standards (Aldrich, 15 standards, 760-1,800,000 Daltons). Gel-filtration chromatography (GFC) was carried out on a Waters chromatograph (three Shodex polyhydroxymethacrylate gel columns OHpak SB-802HQ, SB-802.5HQ, and SB-804HQ columns in series) connected to a Waters 410 RI detector with 50-mM phosphate buffer (pH 7.0, 50 mM NaCl) as an eluent at a flow rate of 0.3 mL/min.

Dynamic light scattering (DLS) measurements were performed on a Zetasizer Nano ZS (Marvern Instruments, Malvern, UK) with a He—Ne laser (633 nm). Non-invasive backscatter method (detection at 173° scattering angle) was used. Correlation data were fitted—using the method of cumulants—to the logarithm of the correlation function, yielding the diffusion coefficient, D. The hydrodynamic diameters ($D_H$) of the nanoparticles (BLs, PILs, and PCLs) were calculated using D and the Stokes-Einstein equation ($D_H=k_BT/3\pi\eta D$, where $k_B$ is the Boltzmann constant, T is the absolute temperature, and q is the solvent viscosity ($\eta$=0.8872 cP for water)). The polydispersity index (PDI) of liposomes—represented as $2c/b^2$, where b and c are first and second order coefficients, respectively, in a polynomial of a semi-log correlation function—was calculated by the cumulants analysis. Size distribution of vesicles was obtained by the non-negative least squares (NNLS) analysis (Stock et al., 1985, J. Polym. Sci. Pt. B Polym. Phys. 23:1393-1447). Unless noted otherwise, all samples were dispersed in 10-mM PIPES solution (pH 7.4, 150 mM NaCl) for DLS measurements. The data reported represent an average of ten measurements with five scans each.

Transmission electron microscopy (TEM) was performed on a Hitachi H8100 microscope operating at an accelerating voltage of 200 kV. All samples were negatively stained with 4-wt % aqueous uranyl acetate. Fluorescence emission spectra were obtained on a Jobin Yvon-SPEX Fluorolog fluorometer ($\lambda_{ex}$=470 nm, $\lambda_{em}$=514 nm).

Example 1

Synthesis of an Exemplary Cholesterol-Terminated Poly(acrylic Acid)

General Materials 2,2,5-Trimethyl-4-phenyl-3-azahexane-3-oxy radical 2 was synthesized using a reported literature procedure (Benoit et al., 1999) 1,2-dipalmitoyl-sn-glycero-3-phosphocholine (DPPC) and 1,2-dioleoyl-sn-glycero-3-[phospho-rac-(1-glycerol)] (sodium salt) (DOPG) were purchased from Avanti Polar Lipids (Alabaster, Ala.). ICP calibration standard solutions of phosphorus (1000 μg/mL P), 1-(3-dimethylaminopropyl)-3-ethylcarbodiimide methiodide (EDC MeI), and all other reagents, buffer mixes, and solvents were purchased from the Aldrich Chemical Company and used as received. Tert-butyl acrylate was stirred over $CaH_2$ under nitrogen and fractionated by vacuum transfer right before use. Nanopure water was obtained from a Millipore system (18.2 MΩ cm resistivity).

For syntheses, HPLC-grade tetrahydrofuran (THF, Fisher Scientific) was dried over neutral alumina via the Dow-Grubbs solvent system (Pangborn et al., 1996, Organometallics 15:1518-1520) installed by Glass Contours (Laguna Beach, Calif.). The solvent was collected under argon, degassed under vacuum, and stored under nitrogen in a Straus flask prior to use. ACS-grade benzene, chloroform, methylene chloride, ethyl acetate, acetone and methanol were obtained from commercial sources (either Fisher Scientific or VWR) used without further purifications. Deuterated solvents (Cambridge Isotope Laboratories) was purchased from commercial sources and used as received. All flash chromatography was carried out using a 56-mm inner diameter column containing 200-mm of silica gel (230-400 mesh, purchased from Sorbent Technologies; Atlanta, Ga.) under a positive pressure of lab air. Spectra/Por Cellulose Ester (CE) dialysis membranes were purchased from Spectrum Laboratories (Rancho Dominguez, Calif.). Liposome extruder and extrusion membranes were purchased from Avanti Polar Lipids (Alabaster, Ala.). Vortexing of solutions was carried out using a Vortex Mixer (American Hospital Supply Corp. McGrow Park, Ill.) set at 5.5 setting.

Preparation of N-tert-Butyl-O-[1-(4-chloromethyl-phenyl)-ethyl]-N-(2-methyl-1-phenyl-propyl)-hydroxylamine (3)

Chloromethyl alkoxyamine initiator 3 was prepared using a modified literature procedure (Dao et al., 1998, J. Polym. Sci. Pol. Chem. 36:2161-2167). To a 100-mL round-bottom flask equipped with a magnetic stirbar was added 2 (1.257 g, 5.0 mmol), p-vinyl benzyl chloride 1 (1.526 g, 10.0 mmol), and a mixture of benzene/ethanol (1:1 v/v, 30 mL). To the resulting solution was then added [(S,S)-(+)-1,2-cyclohexanediamino-N,N'-bis(3,5-di-tert-butylsalicylidene)]manganese(III) chloride (476.4 mg, 0.75 mmol) followed by sodium borohydride (378.3 mg, 10.0 mmol). The reaction mixture was capped with a rubber steptum containing a needle vent and allowed to stir for 15 hours at room temperature with a slow bubbling of air directly into the reaction using a 22-gauge needle (care must be taken with the bubbling rate (~2 bubbles/s) so as not to evaporate the solvent over the length of the reaction).

After the reaction, the solvent was concentrated on a rotary evaporator. The resulting oily crude product was dissolved in dichloromethane (~50 mL) and washed with deionized water (3×50 mL). The organic layer was again concentrated to a minimum on a rotary evaporator and purified by flash chromatography, eluting with 2% ethyl acetate in hexanes. The desired chloromethyl alkoxyamine 3 was obtained as a colorless oil (1.179 g, 63.1% yield). $^1$H NMR (500 MHz, $CDCl_3$, both diastereomers): δ 7.5-7.1 (m, 18H), 4.95 (q+q, 2H, both diastereomers), 4.65 (s, 4H), 3.43 (d, 1H, minor diastereomer), 3.31 (d, 1H, major diastereomer), 2.35 (m, 2H, both diastereomers), 1.65 (d, 3H, minor diastereomer), 1.58 (d, 3H, major diastereomer), 1.33 (d, 3H, minor diastereomer), 1.10 (s, 9H, major diastereomer), 0.95 (d, 3H, major diastereomer), 0.82 (s, 9H, minor diastereomer), 0.59 (d, 3H, minor diastereomer), 0.28 (d, 3H, major diastereomer).

Preparation of N-tert-Butyl-O-[1-(4-iodomethyl-phenyl)-ethyl]-N-(2-methyl-1-phenyl-propyl)-hydroxylamine (4)

To a 50-mL round-bottom flask equipped with a magnetic stirbar was added chloromethyl alkoxyamine 3 (1.789 g, 4.784 mmol) and acetone (20 mL). To the resulting solution was added sodium iodide (2.869 g, 19.14 mmol, 4 equiv) and the reaction mixture was capped with a rubber septum and allowed to stir for 24 hours at room temperature. The sodium chloride side product was remove by gravity filtration, and the filtrate was concentrated on a rotary evaporator. The crude oily product was purified by flash chromatography, eluting with hexanes. The desired iodomethyl akoxyamine 4 was obtained as a colorless oil (1.968 g, 88.3% yield). ESI-MS: m/z=466.0, observed; 465.41, calculated. $^1$H NMR (500 MHz, CDCl$_3$, both diastereomers) δ 7.5-7.1 (m, 18H), 5.35 (t, 2H) 4.90 (q+q, 2H, both diastereomers), 4.55 (s, 4H), 3.55 (m, 2H), 3.40 (d, 1H, minor diastereomer), 3.30 (d, 1H, major diastereomer), 2.40 (m, 2H, both diastereomer), 2.30 (d, 2H), 1.65 (d, 3H, minor diastereomer), 1.58 (d, 3H, major diastereomer), 1.33 (d, 3H, minor diastereomer), 1.05 (s, 9H, major diastereomer), 0.98 (s, 6H), 0.95 (d, 3H, major diastereomer), 0.89 (d, 12H), 0.85 (d, 6H), 0.82 (s, 9H, minor diastereomer), 0.68 (s, 2H), 0.59 (d, 3H, minor diastereomer), 0.28 (d, 3H, major diastereomer).

Preparation of N-tert-Butyl-O-[1-(4-cholesterolmethyl-phenyl)-ethyl]-N-(2-methyl-1-phenyl-propyl)-hydroxylamine (5)

Inside a drybox, sodium hydride (51.5 mg, 2.146 mmol) was added to a 50-mL two-neck flask equipped with a magnetic stirbar and a water-cooled reflux condenser. The flask was capped with a rubber septum, taken out of the drybox, and attached to a Schlenk line and a water line. Anhydrous tetrahydrofuran (20 mL) was then added to make a suspension.

Into a 50-mL Schlenk flask equipped with a magnetic stirbar was added iodomethyl alkoxyamine 4 (500 mg, 1.073 mmol). Into a second Schlenk flask equipped with a magnetic stirbar was added cholesterol (414.9 mg, 1.073 mmol). Both flasks were evacuated and back filled with nitrogen on a 50-mL Schlenk line three times before dry tetrahydrofuran (1 mL for the second flask and 5 mL for the third) were injected via a gas-tight syringe. The cholesterol solution in the second Schlenk flask was then transferred into the NaH suspension using a cannula. The resulting mixture was stirred at room temperature under nitrogen for 20 min when the alkoxyamine solution from the first Schlenk flask was added dropwise to it via a gas-tight syringe. The reaction mixture was next heated at reflux for 5 hours at 60° C. and then transferred into a 50-ml round-bottom flask. After the solvent was evaporated on a rotary evaporator, the resulting oily crude product was dissolved in dichloromethane (~50 mL) and washed with deionized water (3×50 mL). The organic layer was again concentrated to a minimum on a rotary evaporator and purified by flash chromatography, eluting with 1% ethyl acetate in hexanes. The cholesterol-modified alkoxyamine 5 was isolated as a colorless oil (609 mg, 78.3% yield). $^1$H NMR (500 MHz, CDCl$_3$, both diastereomers): δ 7.5-7.1 (m, 18H), 5.35 (t, 2H) 4.90 (q+q, 2H, both diastereomers), 4.55 (s, 4H), 3.55 (m, 2H), 3.40 (d, 1H, minor diastereomer), 3.30 (d, 1H, major diastereomer), 2.40 (m, 2H, both diastereomers), 2.30 (d, 2H), 1.65 (d, 3H, minor diastereomer), 1.58 (d, 3H, major diastereomer), 1.33 (d, 3H, minor diastereomer), 1.05 (s, 9H, major diastereomer), 0.98 (s, 6H), 0.95 (d, 3H, major diastereomer), 0.89 (d, 12H), 0.85 (d, 6H), 0.82 (s, 9H, minor diastereomer), 0.68 (s, 2H), 0.59 (d, 3H, minor diastereomer), 0.28 (d, 3H, major diastereomer). ESI-MS: m/z=724.2, observed; 724.16, calculated.

It was noted that the chloromethyl akoxyamine 3 can also be used in place of 4. The reaction between 3 and the K salt of cholesterol (synthesized via reaction of KH and cholesterol) also works.

Preparation of Cholesterol-Functionalized Poly(acrylic Acid) (6&7)

To a 5-mL conical Pyrex reaction vessel (thick-wall glass used in commercial microwave synthesis, obtained from either Biotage or CEM) equipped with a magnetic stirbar was added a mixture of the cholesterol-attached alkoxyamine 5 (49.4 mg, 68.27 μmol), nitroxide radical 2 (0.86 mg, 3.41 μmol), and tert-butyl acrylate (4.375 g, 34.13 mmol). The resulting solution was sealed with a rubber septum, degassed by three times freeze/thaw cycles using a 18-gauge needle, and heated at 120° C. for 9 hours under nitrogen. After cooling down to room temperature, the reaction content was transferred into a 25-mL round-bottom flask and the remaining monomers were removed by rotary evaporator. The crude rubbery solid product was redissolved in a minimum amount of dichloromethane and then precipitated by addition of a methanol/water (8:2 v/v) mixture. The molecular weight of the cholesterol-attached poly(tert-butyl acrylate) 6 was measured by gel permeation chromatography (GPC). $M_n$=3.8 kDa, DP=24 taking into account the mass of the initiator, $M_w/M_n$=1.097. A DP of 24 was independently obtained by $^1$H NMR integration.

For hydrolysis, the resulting polymer 6 (~190 mg, 50 μmol) was dissolved in dichloromethane (10 mL) and a 5-fold molar excess of trifluoroacetic acid (TFA) was added followed by stirring at room temperature for 15 hours. During hydrolysis, the rubbery PAA slowly precipitated out of the solution. After removal of dichloromethane and TFA by rotary evaporator, the cholesterol-attached poly(acrylic acid) product (Chol-PAA, 7) was dissolved in nanopure water (3 mL) by adjusting the pH to 7.0 with aqueous NaOH (1M) and purified by dialysis (MWCO=2000, 3-mL membrane tube) against nanopure water (14×1000 mL) for a week with water change in every 12 h. After dialysis, water was removed from the product solution (inside the membrane) by lyophilization to give the product as a colorless rubber (23.2 mg, 9.28 μmol, $M_n$=2.5 kDa taking into account the mass of the initiator). The attachment of cholesterol and removal of tert-butyl group were confirmed by $^1$H NMR after hydrolysis. The resulting Chol-PAA was dissolved in nanopure water (1 mL) by adjusting the pH to 7.4 with aqueous NaOH (1M) to give the final concentration of 9.28 mM.

Example 2

Liposome Preparation

Figure 4:
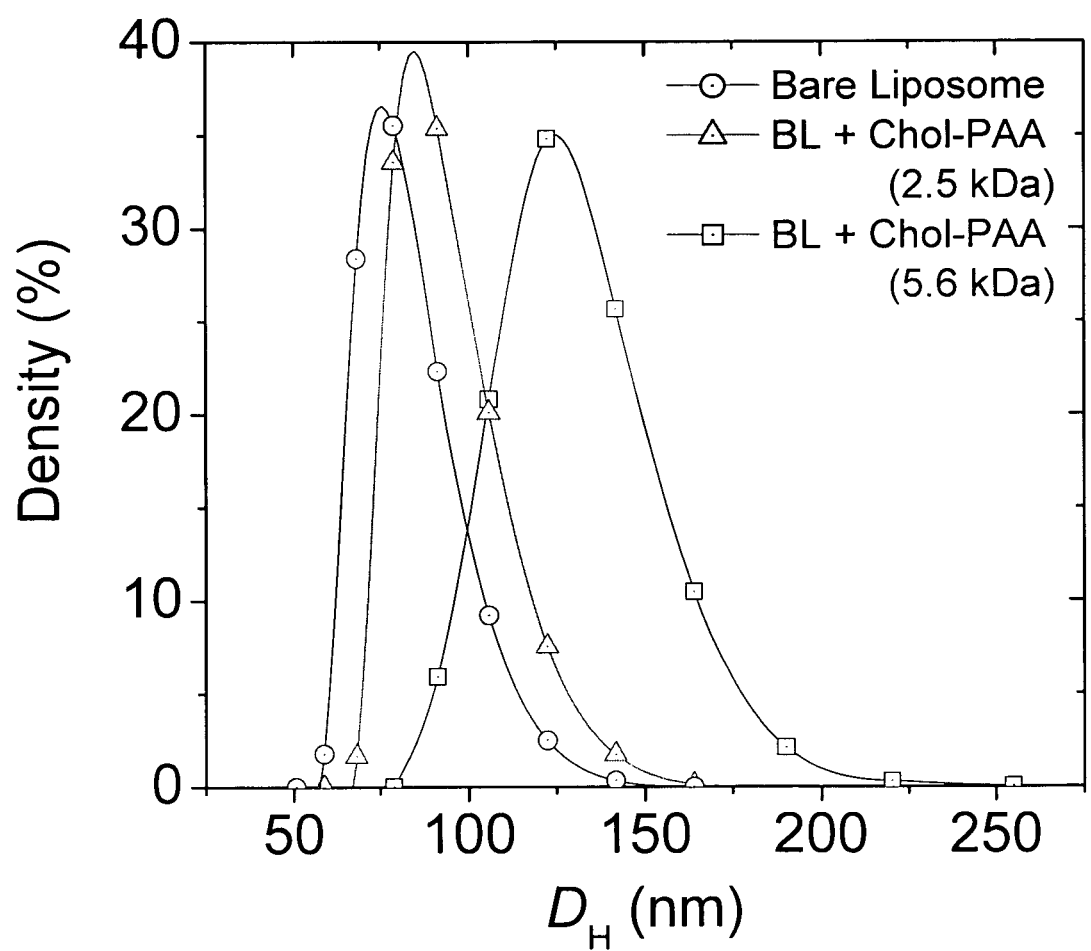
FIG. 4 shows the hydrodynamic diameters ($D_H$) of bare liposomes and polymer-incorporated liposomes measured by dynamic light scattering.

Liposomes were made from a mixture of DPPC/DOPG/Cholesterol (51.4/3.6/45, mol % ratio) using a modification of a general preparative procedure for liposomes. To a glass vial (15×45 mm) was added DPPC (4.55 mg), DOPG (0.35 mg), and cholesterol (2.1 mg), followed by chloroform (0.3 mL) to make a colorless solution. After vortexing (30 sec), the solvent was removed by passing a stream of nitrogen over the solution while the vial was warmed in a 50° C. water bath. The resulting dry film was further dried under vacuum on a Schlenk line (30 mTorr) for one hour. Next, the dry lipid films were hydrated in 10-mM PIPES buffer solution (300 μL, pH 7.4, 150 mM NaCl) followed by vigorous vortex (3-5 min) to form a dispersion of multilamellar vesicles (MLVs). After they were subjected to 10 freeze-thaw cycles, the resulting dispersion of MLVs was extruded ten times through two stacked polycarbonate extrusion membranes (100-nm pore-size) that are maintained at 50° C. on an extruder block (Szoka et al., 1980, Biochim. Biophys. Acta 601:559-571). At the end, the initial vial and syringes were washed with an additional aliquot of PIPES buffer (100 μL) and this wash was also extruded ten times. The combined solution (~400 μL) contain liposomes with a mean hydrodynamic diameter of 82±14 nm (PDI=0.046±0.021) as determined by DLS measurements (FIG. 4). The final concentration of lipids was 19.25 mM (7.7 μmol) as determined by phosphorous ICP-OES.

Example 3

Preparation of Polymer-Incorporated Liposomes (PILS)

To a liposome solution (100 μL, 1.925 μmol), prepared as described above, was added Chol-PAA solution (20.7 μL, 192.5 nmol, 10 mol % relative to the lipid concentration) and incubated at room temperature overnight (Menger et al., 2006, J. Am. Chem. Soc. 128:1414-1415). Free unbound polymers were removed by passing the incubated solution through a Sephadex G-50 column (fraction range: 1,500-30,000 Da, 2 cm×7 cm) that was wet-packed and pre-equilibrated with 10-mM PIPES solution (pH 7.4, 150 mM NaCl). The eluant was also 10-mM PIPES solution and the fractions was collected every 5 drops. The PIL-containing fractions can be easily recognized by their turbidity and combined together (~1.5 mL). The hydrodynamic diameter ($D_H$) of the PIL increased to 93±15 nm (PDI=0.047±0.016) (FIG. 4). The final concentration of lipids was 1.058 mM as determined by phosphorous ICP-OES.

As a comparison, Chol-PAA with a 5.6-kDa $M_n$ was also prepared and combined with the same BLs. DLS measurements of the resulting PILs revealed a mean $D_H$ of 128±22 nm (PDI=0.052±0.021).

For the preparation of polymer-caged liposomes (Example 4), an upper limit for the number of carboxylic acid residues on PILs was calculated from the final concentration of lipids in PILs, assuming 100% incorporation of the Chol-PAA additive. Up to 0.82 mol/mol ratio of cholesterol/phospholipid was reported in human plasma membrane (Lange et al., 1989, J. Biol. Chem. 264:3786-3793; Lange et al., 2004, Proc. Natl. Acad. Sci. 101:11664-11667) and it was observed that up to 35 mol % of the cholesterol-modified PEG-derivatives was inserted into the outer membrane of 100-nm preformed liposome using post-insertion method (Menger et al., 2006). In the present case, maximum cholesterol mol % in outer layer was less than 35 mol %.

Example 4

Preparation of Polymer-Caged Liposomes (PCLs)

EDC-MeI (1.0 mg, 3.365 μmol) was dissolved in 10-mM PIPES buffer (500 μL, pH 7.4, 150 mM NaCl) to give a 6.73-mM EDC-MeI solution. This EDC-MeI solution (300 μL, 2.019 μmol, ~4.0 equiv to the total number of carboxylic acid groups (507.8 nmol) assuming 100% incorporation of the Chol-PAA additive) was added to a disposable culture tube (13 mm×100 mm, Fisher Scientific) containing an aliquot (200 μL, 211.6 nmol) of the previously prepared PIL solution to activate the carboxylic acids in PAA residue outside PILs. After 20 min, 2,2'-(ethylenedioxy)bis(ethylamine) (127.0 nmol, 0.25 equiv to the total carboxylic acid groups for a theoretical 50% crosslinking) was added and the mixture was capped with parafilm and left overnight. Byproducts were removed by dialysis (MWCO=10,000, 1-mL membrane tube) against 10-mM PIPES buffer (6×500 mL, pH 7.4, 150 mM NaCl) for 3 days with buffer change in every 12 h. The final concentration of lipids was 461.8 μM as determined by phosphorous ICP-OES The molecular weights of crosslinked polymer-shell in PCLs and non-crosslinked Chol-PAA anchored on PILs were compared by gel filtration chromatography (FIG. 5). Liposome templates in both PCLs and PILs were broken up by addition of a 5% aqueous solution of Triton X-100 (5 μL) and the resulting solution was manually injected into the gel filtration chromatograph. A calibration curve was obtained from four linear PAA standards (Aldrich Chemicals, molecular weights=2.1, 5.1, 15, 100 kDa) and the molecular weights of samples were calculated from the calibration curve.

For lyophilization, an aliquot (500 μL, 461.8 μM) of the prepared PCL solution was placed into a 5-mL vial and frozen in liquid nitrogen before drying under vacuum (either in a lyophylizer or on a Schlenk line). The residual solid was rehydrated with nanopure water (500 μL) followed by vortexing (10 min). The rehydrated samples were observed by both DLS and TEM (FIG. 6). For $^1$H-NMR measurements, PCLs were prepared in nanopure water and the lyophilized PCLs were then rehydrated in $D_2O$.

Example 5

Calcein Release Assay

Using the same procedure reported above, a dry lipid film was hydrated in an aqueous calcein solution (300 μL, 75 mM, pH was adjusted to 7.4 with aqueous NaOH (1M)) to form the calcein-containing liposomes. Free calcein molecules were separated from the vesicles by Sephadex G-50 column equilibrated with 10-mM PIPES solution (pH 7.4, 150 mM NaCl). Preparations of calcein-containing PILs and PCLs were carried out as described above.

For the plasma stability test, a calcein-containing vesicle solution was mixed with fetal bovine serum in a 1:9 or 5:5 v/v ratio (the concentration of lipid was 36.94 μM) and incubated at 37° C. in a capped 5-mL vial. The fluorescence from the liposome-encapsulated calcein was self-quenched due to its high concentration inside the vesicle. Hence, only the fluorescence from the dye that has leaked out of the ruptured liposome was measured (Allen et al., 1980, Biochim. Biophys. Acta 597:418-426). Aliquots (20 μL) were withdrawn as a function of incubation time, diluted in 10-mM PIPES buffer (980 μL, pH 7.4, 150 mM NaCl), and the calcein leakage was observed by fluorescence spectroscopy. Afterward, 5% aqueous Triton X-100 (5.0 μL) was added to totally break up the liposomes and the total calcein fluorescence was measured to give the 100% release value. The extent of leakage was observed by comparing the release ratio of leaked dye to the maximum release value determined by addition of 5% aqueous Triton X-100 (5.0 μL) to the initial solution (time=0) (Holland et al., 1996).

The percent leakage was calculated as:

$$\% \text{ Leakage} = \frac{(F/F_t^T - F_0/F_0^T)}{(1 - F_0/F_0^T)} \times 100$$

where $F_t$=fluorescence intensity at time t; $F_0$=fluorescence intensity at time zero; $F_t^T$=maximum fluorescence intensity in the presence of Triton X-100 at time t; $F_0^T$=maximum fluorescence intensity in the presence of Triton X-1100 at time zero.

For the acid-induced release assay, a 5-mL vial containing an aliquot of the calcein-containing vesicle solution (1.0 mL, 199.2 µM) was incubated in 50-mM acetate buffer (pH 4.0, 150 mM NaCl) and 50-mM MES buffer (pH 5.5, 150 mM NaCl) at 37° C. and the fluorescence was measured as a function of incubation time as described above.

Example 6

Loading of Doxorubicin into Liposome

To a cylindrical glass vial (15 mm×45 mm) was added DPPC (18.048 µmol), DOPG (1.152 µmol), and cholesterol (12.8 µmol), followed by chloroform (0.5 mL) to make a colorless solution. After vortexing (30 sec), the solvent was removed by passing a stream of nitrogen over the solution while the vial was warmed in a 50° C. water bath. The resulting dry film was further dried under vacuum on a Schlenk line (<30 mTorr) for one hour. Next, the dry lipid films were hydrated in 250-mM aqueous ammonium sulfate solution (500 µL) followed by vigorous vortex (3-5 min) to form a dispersion of multilamellar vesicles (MLVs). After this dispersion were subjected to 10 freeze-thaw cycles, it was extruded ten times through two stacked polycarbonate extrusion membranes (80-nm pore-size) that are maintained at 50° C. The excess ammonium sulfate outside liposome was removed by Sephadex G-50 (10 mL) gel-filtration chromatography pre-equilibrated with 150 mM NaCl solution. To the collected liposome solution (~600-800 µL of a solution with 4 mM lipid concentration) was added doxorubicin (DXR, 0.3 equiv of the total lipid content) followed by incubation at 50° C. for 24 h. The excess DXR outside of the liposome was then removed by Dowex 50wx4 cation-exchange resin. The loading of the Doxorubicin was determined by breaking up the DXR-loaded liposome in reduced Triton X-100 and measuring the dissolved doxorubicin concentration using UV-vis spectroscopy. The resulting DXR-loaded liposomes can then be subjected to the PCL fabrication process as described above.

Example 7

Synthesis of Propargyl-Modified Crosslinker

The propargyl-modified cross-linker was synthesized using a solid-phase methodology on O-bis(aminoethyl)ethylene glycol trityl resin using a fluorenylmethoxycarbonyl (Fmoc)-based double coupling strategy. On a CS-Bio peptide synthesizer, $N_\alpha$-Fmoc-L-2-propargylglycine was first coupled to the resin mediated by O-(Benzotriazol-1-yl)-N,N,N',N'-tetramethyluronium hexafluorophosphate (HBTU). After deprotection of the Fmoc carbamate group (by the addition of 20% v/v piperidine in DMF), subsequent coupling of {2-[2-(Fmoc-amino)ethoxy]ethoxy}acetic acid with HBTU was carried out. The synthesized cross-linker was detached from the resin using trifluoroacetic acid and was purified by preparative reverse phase HPLC (Agilent 1100 instrument with BioSep-SEC-S2000 column 300×21.2 mm, 2 mL/min flow rate). IR($CH_2Cl_2$): 2934, 1682, 1539, 1203, 1136, 837, 800, 721 $cm^{-1}$. ESIMS: m/z=389.92 observed for $M^{2+}$, 388.23 calculated. The resulting propargyl-modified crosslinker can then be used in place of the 2,2'-(ethylendioxy)bis(ethylamine) crosslinker in the aforementioned PCL fabrication process.

Example 8

Synthesis of the Azido-PEG-Folate "Click" Targeting Group

Azido-PEG-folate was synthesized by reacting commercially available azido-PEG-amine (Sigma-Aldrich, 456.1 µmol) with folic acid (Sigma-Aldrich, 547.3 µmol) in a dimethylsulfoxide solution (5 mL) containing dicyclohexylcarbodiimide (547.3 µmol) and 4-(dimethylamino)pyridine (45.6 µmol). The reaction mixture was stirred overnight in the dark at room temperature during which time a dicyclohexylurea precipitate formed. After the urea byproduct was removed by filtration, the product was precipitated by addition of an excess amount of cold diethyl ether. The precipitated crude product was purified by silica gel flash chromatography, eluting with a stepwise gradient of methanol (20 to 80% v/v) in chloroform that has been modified with triethylamine (0.1% v/v). IR(KBr): 3295, 2114, 1697, 1609, 1514, 1304, 1109 $cm^{-1}$. ESIMS: m/z=862.38 observed for $M^+$; 861.40 calculated. The concentration of folic acid was determined by quantitative UV spectrometry of azido-PEG-folate in water using the extinction coefficient ($\epsilon$) of 27022 $M^{-1}$ $cm^{-1}$ at a $\lambda_{max}$ of 278 nm.

Example 9

Conjugation of Azido-PEG-Folate to PCLs by Click Chemistry

To a solution of the propargyl-modified PCL (570 µL of a 2.169 mM solution) containing azido-PEG-folate (24.72 nmol, ~1 mol % of the total lipid content) and $CuSO_4.5H_2O$ (2 mM), was added a freshly prepared sodium ascorbate solution (1.2 mg in 300 µL of water, 6.18 µmol) and the reaction mixture was stirred at room temperature for 12 h. The resulting folate-conjugated PCL solution was purified by Sephadex G-50 (10 mL) gel-filtration chromatography that has been pre-equilibrated with HEPES-buffered (20 mM) NaCl solution (150 mM, pH 7.4).

Example 10

Cytotoxicity Study

KB cells were continuously cultured in folic acid-free medium supplemented with 10% heat-inactivated fetal bovine serum at 37° C. in a humidified atmosphere containing 5% $CO_2$. The cells were seeded into several 48-well plates at 100,000 cells per well. The plates were then returned to the incubator and the cells were allowed to grow to confluence for 24 h. The media in the wells were replaced with the pre-prepared growth medium-drug-loaded PCL mixture (200 µL of solution at the appropriate Doxorubicin concentrations). The PCL-treated cell cultures were then further incubated for 2 h in a humidified atmosphere containing 5% $CO_2$ at 37° C., after which the growth medium—drug-loaded PCL mixture was removed by aspiration. The remaining cell layers were washed with PBS buffer (2×250 µL) followed by replacement with fresh growth media (200 µL). The plates were then returned to the incubator and maintained in a humidified atmosphere containing 5% $CO_2$ at 37° C. for a further 48 h. The viable cells were then counted by Guava ViaCount Assay.

All publications and patents mentioned in the present application are herein incorporated by reference. Various modification and variation of the described methods and compositions of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

We claim:

1. A pH-responsive stable polymer-caged liposome comprising a bilayer and cholesterol-terminated, crosslinked poly(acrylic acid), wherein the cholesterol of said cholesterol-terminated poly(acrylic acid) is anchored in said bilayer, and wherein said cholesterol-terminated poly(acrylic acid) forms a polymer cage around said bilayer to form a polymer-caged liposome.

2. The pH-responsive stable polymer-caged liposome of claim 1, wherein said pH-responsive stable polymer-caged liposome is a delivery system for a payload.

3. The pH-responsive stable polymer-caged liposome of claim 2, wherein said payload is selected from the group consisting of: a drug, a small molecule, an inorganic solid, a polymer, a biopolymer, a nucleic acid, and a peptide.

4. The pH-responsive stable polymer-caged liposome of claim 1, further comprising a targeting ligand.

5. The pH-responsive stable polymer-caged liposome of claim 1, further comprising a detectable molecule.

6. The pH-responsive stable polymer-caged liposome of claim 1, further comprising a drug molecule.

7. A composition comprising the pH-responsive stable polymer-caged liposome of claim 1.

8. A method for transfecting eukaryotic cells in vitro comprising:
   a) providing:
      i) a pH-responsive, stable polymer-caged liposome of claim 1,
      ii) a eukaryotic cell,
      iii) an agent selected from the group consisting of: a nucleic acid, a peptide, a small molecule, a drug, an inorganic solid, a polymer, or a biopolymer;
   b) complexing said liposome with said agent; and,
   c) transfecting said complexed liposome into said eukaryotic cell.

9. The method of claim 8, wherein said transfecting is performed in mammalian cells.

10. A delivery system comprising a liposome comprising cholesterol-terminated poly(acrylic acid), wherein the cholesterol of said cholesterol-terminated polyacrylic acid is anchored in said liposome and wherein said poly(acrylic acid) has been crosslinked by a bifunctional crosslinking molecule.

11. The delivery system of claim 10, wherein said delivery system is pH-responsive.

12. The delivery system of claim 10, wherein said liposome comprises a payload selected from the group consisting of: a drug, small molecule, inorganic solid, polymers, biopolymers, a nucleic acid, and a peptide.

13. The delivery system of claim 10, further comprising a targeting ligand.

14. The delivery system of claim 10, further comprising a detectable entity.

15. The delivery system of claim 10, further comprising a drug molecule.

* * * * *

UNITED STATES PATENT AND TRADEMARK OFFICE
CERTIFICATE OF CORRECTION

PATENT NO.        : 8,821,922 B2                                                    Page 1 of 1
APPLICATION NO.   : 12/135828
DATED             : September 2, 2014
INVENTOR(S)       : Sang-Min Lee et al.

It is certified that error appears in the above-identified patent and that said Letters Patent is hereby corrected as shown below:

In the Specification

In Column 1, lines 7-14, the federal funding should read as follows:

--This invention was made with government support under grant numbers DMR-0094347 and EEC-0647560 awarded by the National Science Foundation and grant numbers U54CA119341 and P30CA060553 awarded by the National Institutes of Health. The government has certain rights in the invention.--

Signed and Sealed this
Eleventh Day of November, 2014

Michelle K. Lee
*Deputy Director of the United States Patent and Trademark Office*